US008524445B2

(12) United States Patent
Sun et al.

(10) Patent No.: US 8,524,445 B2
(45) Date of Patent: Sep. 3, 2013

(54) DETECT AND IDENTIFY VIRUS BY THE MICROWAVE ABSORPTION SPECTROSCOPY

(75) Inventors: Chi-Kuang Sun, Taipei (TW); Tzu-Ming Liu, Keelung (TW); Hung-Pin Chen, Kaohsiung county (TW)

(73) Assignee: National Taiwan University, Taipei (TW)

( * ) Notice: Subject to any disclaimer, the term of this patent is extended or adjusted under 35 U.S.C. 154(b) by 1323 days.

(21) Appl. No.: 12/050,894

(22) Filed: Mar. 18, 2008

(65) Prior Publication Data

US 2009/0237067 A1 Sep. 24, 2009

(51) Int. Cl.
*C12Q 1/70* (2006.01)
*G01N 27/00* (2006.01)

(52) U.S. Cl.
USPC .......................................... 435/5; 324/71.1

(58) Field of Classification Search
USPC .......................................... 324/71.1; 435/5
See application file for complete search history.

(56) References Cited

U.S. PATENT DOCUMENTS

| | | | | |
|---|---|---|---|---|
| 5,481,196 | A * | 1/1996 | Nosov | 324/637 |
| 2003/0204130 | A1* | 10/2003 | Colston et al. | 600/300 |
| 2008/0161674 | A1* | 7/2008 | Monro | 600/410 |

OTHER PUBLICATIONS

Stephanidis et al (2007) Biophys J, 93:1354-1359.*
Office Action of TW application No. 097107939, dated Feb. 21, 2012.
Siegel, Terahertz Technology, IEEE Transactions on Microwave Theory and Techniques, 2002, p. 910-928, vol. 50.
The characteristic of THz irradiation and its application in image and material science, 2007, http://research.ncku.edu.tw/re/articles/c/20071005/3.html.
F.H. Westheimer; Why Nature Chose Phosphates; Journal; Mar. 6, 1987; pp. 1173-1178; vol. 235; Science.
Horace Lamb; On the Vibrations of an Elastic Sphere; Journal; 1882; pp. 189-212.
Eugene Duval; Far-infrared and Raman vibrational transitions of a solid sphere; Journal; Sep. 1, 1992; pp. 5795-5797; vol. 46, No. 9; Physical Review B; Rapid Communications.
Daniel B Murray et al.,; Far-Infrared Absorption by Acoustic Phonons in Titanium Dioxide Nanopowders; Journal; 2006; pp. 92-98; vol. 1, No. 1; Journal of Nanoelectronics and Optoelectronics; American Scientific Publishers; USA.
B. Stephanidis et al.,; Elastic properties of viruses; Journal; May 25, 2007; pp. 1-27; Biophys J BioFAST; The Biophysical Society.
Mina Talati et al.,; Acoustic phonon quantization and low-frequency Raman spectra of spherical viruses; Journal; 2006; pp. 1-6; vol. 73; Physical Review; The American Physical Society.
Matthew A Cooper et al.,; Direct and sensitive detection of a human virus by rupture event scanning; Journal; Sep. 2001; pp. 833-835; vol. 19; Research Article; Nature Biotechnology; Nature Publishing Group.

(Continued)

*Primary Examiner* — N. C. Yang
*Assistant Examiner* — Richard Moerschell
(74) *Attorney, Agent, or Firm* — WPAT, P.C.; Anthony King

(57) ABSTRACT

The present invention discloses microwave resonant absorption (MRA) of viruses through dipolar coupling to viral confined acoustic modes. The unique geometrical and mechanical properties of viruses can be reflected by the MRA frequencies, MRA linewidth, and the absorption selection rules of high-order acoustic modes. Combined these spectral characteristics with the mature microwave technology, this invention provides a novel physical mechanism to develop non-affinity-based rapid detection and identification of viruses. It can be applied in preliminary characterization on unknown or mutant viruses.

6 Claims, 3 Drawing Sheets

(56) References Cited

OTHER PUBLICATIONS

Aurel Ymeti et al.,; Fast, Ultrasensitive Virus Detection Using a Young Interferometer Sensor; Journal; 2007; pp. 394-397; vol. 7, No. 2; Nano Letters; The American Chemical Society.

S.J. Webb et al.,; Absorption of Microwaves by Microorganisms; Journal; Jun. 21, 1969; pp. 1199-1200; vol. 222; Nature.

S.J. Webb et al.,; Microwave Absorption by Normal and Tumor Cells; Journal; Apr. 29, 1971; pp. 72-74; vol. 174; Science.

G.S. Edwards et al.,; Resonant Microwave Absorption of Selected DNA Molecules; Journal; Sep. 24, 1984; pp. 1284-1287; vol. 53, No. 13; Physical Review Letters; The American Physical Society.

W. Grundler et al.,; Sharp Resonances in Yeast Growth Prove Nonthermal Sensitivity to Microwaves; Journal; Sep. 26, 1983; pp. 1214-1216; vol. 51, No. 13; Physical Review Letters; The American Physical Society.

Chung-Hsiung Wang et al.,; A New Picorna-like Virus, PnPV, Isolated from Ficus Transparent Wing Moth, *Pernia nuda* (Fabricius); 1999; pp. 62-68; vol. 74; Journal of Invertebrate Pathology; Academic Press.

Jyh-Ming Tsai et al.,; Identification of the Nucleocapsid, Tegument, and Envelope Proteins of the Shrimp White Spot Syndrome Virus Virion; Journal; Mar. 2006; pp. 3021-3029; vol. 80, No. 6; Journal of Virology; American Society for Microbiology.

Jyh-Ming Tsai et al.,; Genomic and Proteomic Analysis of Thirty-Nine Structural Proteins of Shrimp White Spot Syndrome Virus; Journal; Oct. 2004; pp. 11360-11370; vol. 78, No. 20; Journal of Virology; American soceity for Microbiology.

L.L. Van Zandt; Resonant Microwave Absorption by Dissolved DNA; Journal; Oct. 20, 1986; pp. 2085-2087; vol. 57, No. 16; Physical Review Letters; The American Physical Society.

Takeshi Noda et al.,; Architecture of ribonucleoprotein complexes in influenza A virus particles; Journal; Jan. 26, 2006; pp. 490-492; vol. 439; Letters; Nature Publishing Group.

\* cited by examiner

DETECT AND IDENTIFY VIRUS BY THE MICROWAVE ABSORPTION SPECTROSCOPY

FIELD OF THE INVENTION

The present invention relates to a novel physical method to develop non-affinity based rapid detection or identification of viruses through microwave resonant absorption.

BACKGROUND OF THE INVENTION

The cores of most viruses have inherent negative charges due to the phosphate group in genomes (Westheimer, F. H. Why nature chose phosphates. *Science* 235, 1173-1178 (1987)). In contrast, the amino acids of viral capsids or envelopes have complex charge distributions on the surface of viruses. Such core-shell charge separation paves the road for the dipolar coupling between electromagnetic waves and confined acoustic vibrations. The MRA processes should thus occur in viruses when the confined acoustic vibration moves the charges and changes their dipole moments. For spherical viruses, such a vibrational mode is the spheroidal (SPH) mode with an angular momentum l=1. (Lamb, H. On the vibrations of an elastic sphere. *Proc. London Math. Soc.* 13, 189-212 (1882), Duval, E. Far-infrared and Raman vibrational transitions of a solid sphere: Selection rules. *Phys. Rev. B* 46, 5795-5797 (1992)) Due to its Raman inactive nature, the l=1 SPH mode has been rarely studied experimentally, for example, there is no published report on its measured oscillation frequency versus size. On the other hand, both the theoretically calculated [SPH, l=1, n=0] and [SPH, l=1, n=1] dipolar modes (See FIG. 1a) have relative displacement between the core (indicated by light-colored arrows) and shell (indicated by dark-colored arrows) (Murray, D. B. et al. Far-infrared absorption by acoustic phonons in Titanium dioxide nanopowders. *J. Nanoelectron. Optoelectron.* 1, 92-98 (2006)), which should induce MRA through the core-shell charge structure of a nanoparticle, including viruses. By assuming a virus as a homogeneous sphere with elastic parameters close to the Satellite Tobacco Mosaic Virus crystal, (Stephanidis, B., Adichtchev, S., Gouet, P., McPherson, A. Mermet, A. Elastic properties of viruses. *Biophys. J.* 93, 1354-1359 (2007)) one can estimate the frequency of the [SPH, l=1, n=0] mode for a 30 nm virus to be around 40 GHz. The frequencies of the dipolar modes are determined by the longitudinal sound velocity $V_L$, transverse sound velocity $V_T$, and the radius of viruses R. (Lamb, H. On the vibrations of an elastic sphere. *Proc. London Math. Soc.* 13, 189-212 (1882) Assuming $V_L/V_T$ 1 8 2 for viruses (Talati, M. & Jha, K. Acoustic phonon quantization and low-frequency Raman spectra of spherical viruses. *Phys. Rev. E* 73, 011901 (2006)), the eigen frequencies are expected to be proportional to $V_L/R$ For most viruses, their sizes range from 10 nm to 300 nm and their $V_L$ doesn't change too much, thus making the frequency of the dipolar modes falls in the microwave range.

Except for spheres, rods and filaments are among the other shapes most commonly found in viruses. The charge separation between the core and two tips could also induce MRA related to the longitudinal acoustic standing waves. However, different from the SPH confined acoustic modes in a sphere, not all orders of the confined longitudinal acoustic waves in a rod-like structure can induce MRA. FIG. 1b illustrates that only standing waves with the mode order N equal to 2(2m+1) have relative motion between two ends and the center of the rod, where m=0, 1, 2 . . . . It is expected that the selection rule of the high-order-acoustic-mode absorption varies with the shape of viruses.

Besides, the homogeneous broadening linewidth of the MRA can further provide information regarding the mechanical properties of the virus. Considering small acoustic impedance contrast (Westheimer, F. H. Why nature chose phosphates. *Science* 235, 1173-1178 (1987)) between water and a virus, the theoretically predicted mechanical quality factor of the viral confined acoustic modes is much less than one (Talati, M., Jha, P. K. Acoustic phonon quantization and low-frequency Raman spectra of spherical viruses. *Phys. Rev. E* 73, 011901 (2006)). In contrast, the standard deviation of the viral size is typically <±5%, which makes the MRA quality factor $Q_{MRA}$ larger than 10. Therefore, the microwave spectral linewidth of a virus should be dominated by the homogeneous broadening, making MRA bandwidth another useful indicator for the mechanical properties of viruses.

a. Displacement of the [SPH, l=1, n=0] and [SPH, l=1, n=1] dipolar modes in a free homogeneous sphere. The light-colored arrows and dark-colored arrows indicate the local displacement of the core and shell of a nanosphere, respectively.

b. Displacement of the longitudinal standing waves in a rod. Solid and dashed yellow curve represent the distribution of displacement when both ends have largest displacement. Dark-colored and light-colored arrows indicate the direction of displacement at ends and center of the rod, respectively. For the mode order N=1, 3, 5, 7, the center of rod becomes a node of standing waves, which is indicated by a solid circle.

c. Schematic diagram of the microwave resonant absorption measurement. We dropped 1 µl virus-containing solution on a co-planar waveguide (CPW) with a quartz substrate. The gap width between ground and signal stripes (center gold stripe) was 26 µm. The width and the length of the signal stripe line were 130 µm and 4 mm, respectively. The gold metal layer had a thickness of 700 nm. The direction and strength of electric field are schematically indicated by the direction and length of arrows. As shown in the figure, the electromagnetic waves were confined around the electrodes and interacted with the viruses (solid circles).

Figure 2:
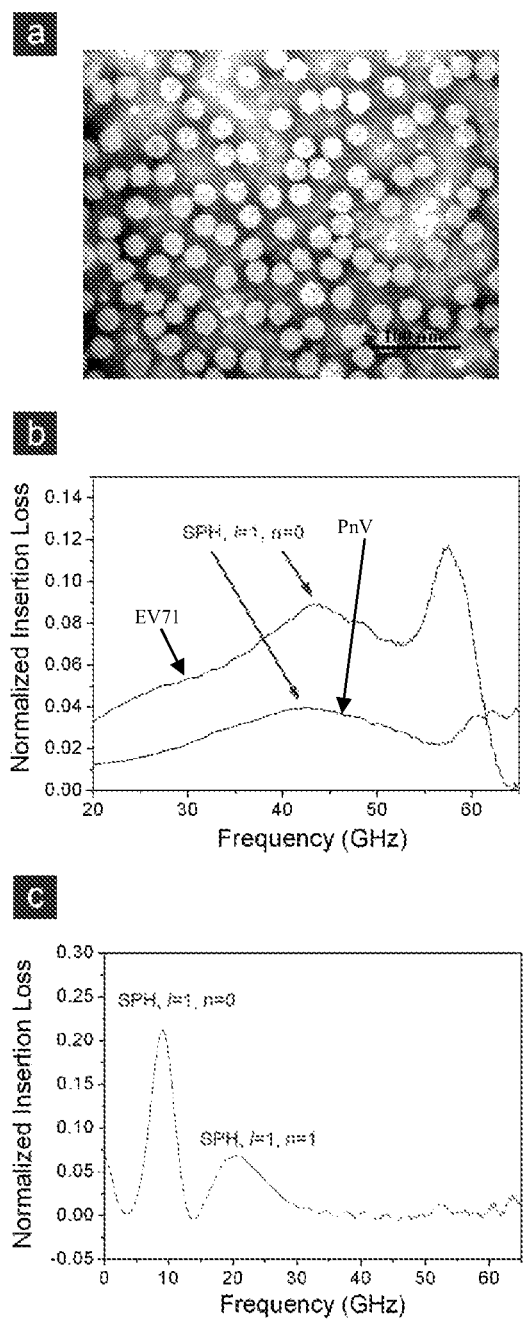

FIG. 2 illustrates microwave resonant absorption of spherical viruses.

a. Negative contrast electron micrograph of isometric particles of Perina nuda viruses (PnV). The viral particles are roughly spherical with a diameter of 29.5±0.5 nm.

b. The MRA spectra of PnV and enterovirus 71 (EV71). The MRA corresponding to the [SPH, l=1, n=0] mode is indicated by arrows.

c. The MRA spectrum of influenza A viruses. Not only [SPH, =1, n=0] but also [SPH, l=1, n=1] modes are dipolar active.

Figure 3:
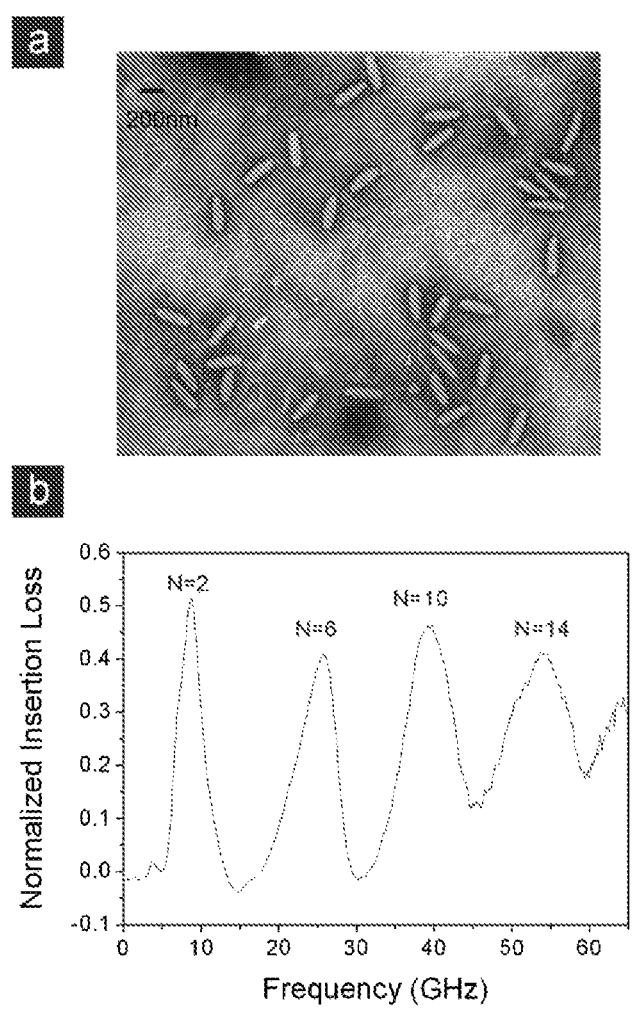

FIG. 3 illustrates microwave resonant absorption of the white spot syndrome virus (WSSV).

a. Negative contrast electron micrograph of WSSV. The average rod length and rod diameter are 320 nm and 115 nm, respectively. The standard deviation of size is ±5%.

b. The MRA spectrum of WSSV, showing the absorption peaks corresponding to mode order N=2, 6, 10, 14.

SUMMARY OF THE INVENTION

The present invention provides a virus spectrum established by using microwave resonant absorption (MRA) comprising MRA frequency; MRA linewidth; and the absorption selection rules of high-order acoustic mode.

The present invention also provides a method for establishing a virus spectrum of said invention.

The present invention further provides a method for detecting or identifying viruses by using virus spectrum of said invention.

DETAILED DESCRIPTION OF THE INVENTION

The MRA spectrum can not only reflects the geometrical and mechanical properties of viruses but can also be a useful fingerprint to uniquely determine the type of viruses without labeling. It is much faster than using labor intensive PCR processes. Compared with other affinity-based virus sensors (Cooper, M. A. et al. Direct and sensitive detection of a human virus by rupture event scanning. *Nature Biotech.* 19, 833-837 (2001), Ymeti, A. et al. Fast, ultrasensitive virus detection using a Young interferometer sensor. *Nano Lett.* 7, 394-397 (2007)), our solution requires no antibody and can be applied in preliminary examination on unknown or mutant viruses. Regarding the sensitivity of quantification, with an average microwave power of −40 dBm and with a scan rate of 1/15 Hz, our simple CPW circuits can at best sense 375 virions in the WSSV's case. The detection sensitivity could be much further improved simply by adopting high power microwave sources, with longer data acquisition time, by using high-Q microwave resonators, and by properly incorporating microfluidic channels. It is also interesting to notice that, from a quantum mechanical point of view, our discovered MRA process is a perfect conversion of a photon (electromagnetic waves) in to a phonon (acoustic oscillation) of the same frequency with 100% quantum efficiency, in sharp contrast to the Raman based process.

The present invention discloses the microwave resonant absorption of viruses through the dipolar coupling to confined acoustic modes. Unlike previously reported molecule-induced MRA (Webb, S. J., Booth, A. D. Absorption of microwaves by microorganisms. *Nature* 222, 1199-1200 (1969), Webb, S. J., Booth, A. D. Microwave absorption by normal and tumor cells. *Science* 174, 72-74 (1971), Edwards, G. S., Davis, C. C., Saffer, J. D., Swicord, M. L. Resonant microwave absorption of selected DNA molecules. *Phys. Rev. Lett.* 53, 1284-1287 (1984)), this acoustic-phonon-induced MRA is highly size and shape sensitive. The unique geometrical and mechanical properties of a virus can thus be reflected by the MRA frequency, MRA linewidth, and the selection rule of the high-order-acoustic-mode absorption. This invention is anticipated to be a starting point to achieve rapid and sensitive microwave detection and non-contact imaging of viruses. Viruses could be characterized and identified even without the help of antibody. With these evidences on the efficient resonant energy transfer with specific microwave frequencies, the function of viruses could probably be selectively affected through a narrow-band microwave source (Grundler, W., Keilmann F. Sharp resonances in yeast growth prove nonthermal sensitivity to microwaves. *Phys. Rev. Lett.* 51, 1214-1216 (1983)).

Accordingly, the present invention discloses a virus spectrum established by using microwave resonant absorption (MRA) comprising MRA frequency; MRA linewidth; and the absorption selection rules of high-order acoustic modes. Then MRA is induced through the dipolar mode between the core and shell inherent charge structure of a virus.

In MRA characteristics, the MRA frequency; MRA linewidth and the absorption selection rules of high-order acoustic mode respectively represent the size; the constituent and the shape of virus.

The present invention provides a method for establishing a virus spectrum of said invention, comprising: (1) preparing a sample containing a known virus; (2) applying microwave with various frequencies to the sample; (3) inducing microwave resonant absorption (MRA) under a dipolar acoustic mode of the sample; and (4)recording an MRA spectrum.

In a preferred embodiment of the present invention, the known virus include, but are not limited to, Perina nuda viruses (PnV), influenza A viruses, bacillary white spot syndrome viruses (WSSV), and *enterovirus* 71 (EV71).

The present invention also provides a method for detecting or identifying a virus by using a virus spectrum, comprising: (1) preparing a material to be detected; (2) applying microwave with various frequencies to the material to be detected; (3) inducing MRA under a dipolar acoustic mode of the material to be detected; (4) recording an MRA spectrum and (5) comparing the MRA spectrum of the detected material with a virus dipolar mode acoustic spectrum, thereby identifying the virus.

In a preferred embodiment of the present invention, the material to be detected includes, but is not limited to, a biological sample from a subject.

EXAMPLES

The examples below are non-limiting and are merely representative of various aspects and features of the present invention.

Virus Sample

Preparation of Perina Nuda Virus (PnV)

The PnV viral particles were purified from infected NTU-PN-HH cell lines (Wang, C. H., Wu, C. Y., Lo, C. F. A new picorna-like virus, PnPV, isolated from Ficus Transparent Wing Moth, Perina nuda (Fabricius). *J. Invertebr. Pathol.* 74, 62-68 (1999)) and dissolved in Tris buffer (pH=7.2).

Preparation of Purified Influenza A Virus

Madin-Darby canine kidney (MDCK) cells were grown in Dulbecco's modified Eagle's medium (DMEM) supplemented with 10% fetal bovine serum (FBS), penicillin [100 U/ml], and streptomycin [100 μg/ml]. They were incubated at 35° C. with 5% $CO_2$. A human influenza A H1N1 subtype strain, A/Tainan/N39/06, was grown in MDCK cells with serum-free DMEM containing 0.2 μg/ml trypsin. Approximately 1000 ml virus culture suspension was collected and the cellular debris was removed by a centrifugation at 3000×g for 30 minutes. Supernatant was then centrifuged for 6 hours at 80,000×g in an ultracentrifuge tube of 10 ml capacity (Backman type 70 Ti tube). The pellet was carefully resuspended with 1 ml PBS containing 1% glutaraldehyde, and then centrifuged for 10 min at 2000×g. The supernatant was collected and loaded on 7 ml of 5-50% (w/w) linear cesium chloride solution in an ultracentrifuge tube. The sample was ultracentrifuged for 20 hours at 120,000×g, and then the gradients were harvested for further test.

Preparation of Purified White Spot Syndrome Virus (WSSV) Virions

Following the method of Tsai, (Tsai, J. M. et al. Identification of the Nucleocapsid, Tegument, and Envelope Proteins of the Shrimp White Spot Syndrome Virus Virion. *J. Virol.* 80, 3021-3029 (2006).) healthy *Procambarus clarkii* crayfishes were infected by hemolymph which was collected from WSSV-infected *Penaeus monodon*. After 1 week, the intact virions in the crayfish hemolymph were purified as described previously (Tsai, J. M. et al. Genomic and proteomic analysis of 39 structural proteins of shrimp white spot syndrome virus. *J. Virol.* 78, 11360-11370 (2004)), (Tsai, J.-M. et al. Identification of the Nucleocapsid, Tegument, and Envelope Proteins of the Shrimp White Spot Syndrome Virus Virion. *J. Virol.* 80, 3021-3029 (2006)). Briefly, after centrifuged the WSSV infected hemolymph at 1,500×g for 10 min, the supernatant was layered on the top of sucrose solution (35% wt/vol in 50 mM Tris buffer, pH 7.5) and ultracentrifuged at 89,000×g for 1 hour at 4° C. The pellet was resuspended and subjected to a 35 to 65% sucrose gradient ultracentrifugation (89,000×g for 2 hours at 4° C). The virus bands were then collected, mixed with Tris buffer and ultracentrifuged at 89,000×g for 1 hour at 4° C. to repellete the WSSV virions. The finial pellet, WSSV intact virions, was dissolved in Tris buffer.

Preparation of Purified *Enterovirus* EV71 Virions

Rhabdomyosarcoma (RD) cells were grown in Dulbecco's modified Eagle's medium (DMEM) supplemented with 10% fetal bovine serum (FBS), penicillin [100 U/ml], and streptomycin [100 μg/ml]. They were incubated at 35° C. with 5% $CO_2$. A human *enterovirus* EV71 strain, N1612/00/TW, was grown in RD cells with DMEM containing 10% FBS. Approximately 100 ml virus culture suspension was collected and the cellular debris was removed by centrifugation at 3000×g for 30 minutes. The remaining processes were the same as that of Influenza A viruses.

Method

Figure 1:
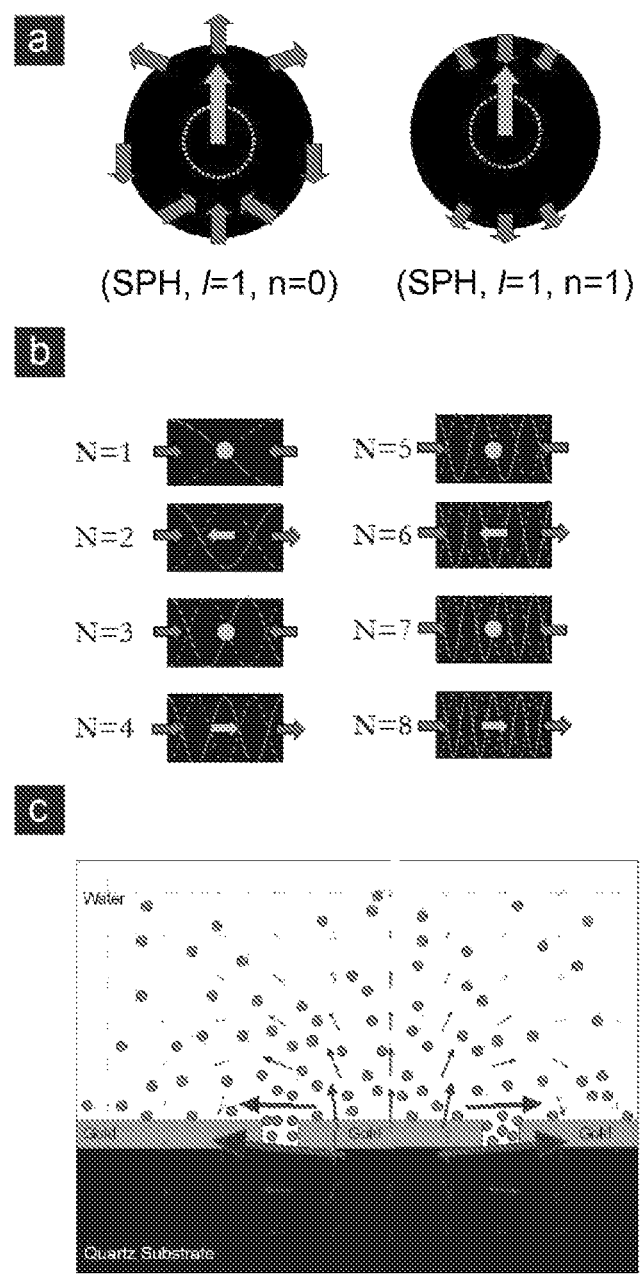
FIG. 1 illustrates dipolar active confined acoustic modes and microwave resonant absorption (MRA) measurement.

To perform MRA spectral measurements, these viruses were cultured, isolated, purified, and then preserved in Tris or Phosphate Buffer Saline (PBS) buffer liquids. In each measurement, we took 1 μl viral solution by a micropipette and uniformly dropped it on the midst of a coplanar waveguide (CPW) circuit (See FIG. 1c) designed for the guiding of 40 MHz~80 GHz electromagnetic waves with high transmission. The guided microwaves can thus incident on the virus-containing solution. The reflection $S_{11}$ and transmission $S_{21}$ parameters of the CPW circuit were simultaneously recorded with a standard (40 MHz-65 GHz) network analyzer. The insertion power loss can be evaluated by $1-|S_{11}|^2-|S_{21}|^2$. As a control, the insertion loss spectra of the corresponding buffer liquids with the same volume were also measured on the same device. By comparing the microwave insertion loss spectra of the buffer solutions with and without viruses, the corresponding MRA spectra of viruses can be obtained.

Results

PnV

The PnV have a narrow size distribution of 29.5±0.5 nm with a nearly spherical symmetry (See FIG. 2*a*). The PnV particles were purified (Wang, C. H., Wu, C. Y., Lo, C. F. A new picorna-like virus, PnPV, isolated from Ficus Transparent Wing Moth, Perina nuda (Fabricius). *J. Invertebr. Pathol.* 74, 62-68 (1999)) and dissolved in Tris buffer with a number density of $3.3\times10^{10}$/μl. In the measured MRA spectrum of PnV (FIG. 2*b*), there is a 42-GHz absorption peak with additional 2~4% loss. With a frequency close to the above mentioned estimation, this observed microwave attenuation could thus be attributed to the MRA through the [SPH, l=1, n=0] mode of PnV, with a $V_L$ of 1920 m/s. Because the transverse velocity of water is zero and the displacement of the [SPH, l=1, n=0] mode has shear component on the surface (Murray, D. B. et al. Far-infrared absorption by acoustic phonons in Titanium dioxide nanopowders. *J Nanoelectron. Optoelectron.* 1, 92-98 (2006)), the corresponding acoustic impedance contrast between water and virus should be higher than that of the [SPH, l=0] modes (Talati, M., Jha, K. Acoustic phonon quantization and low-frequency Raman spectra of spherical viruses. *Phys. Rev. E* 73, 011901 (2006)). Moreover, there are hydration layers on the surface of PnV, which make the viscous damping by the water less effective (Van Zandt, L. L. Resonant microwave absorption by dissolved DNA. *Phys. Rev. Lett.* 57, 2085-2087 (1986)). As we expected, the 42-GHz MRA peak has a quality factor $Q_{MRA}$=4.2, which is higher than that of the pure radial [SPH, l=0] modes (Talati, M., Jha, K. Acoustic phonon quantization and low-frequency Raman spectra of spherical viruses. *Phys. Rev. E* 73, 011901 (2006)). Since the size variation of PnV is smaller than 2%, the homogeneous mechanical properties dominated the linewidth of MRA.

Influenza A Viruses

The diameter of the studied influenza A viruses is typically 100 nm with a ±3% standard deviation (Noda, T. et al. Architecture of ribonucleoprotein complexes in influenza A virus particles. *Nature* 439, 490-492 (2006)). Because this virus is contagious to human, we inactivated the virus by glutaraldehyde. With a larger virus size, the MRA frequency related to the [SPH, l=1, n=0] mode should shift downward to lower frequency was expected. As shown in FIG. 2*c*, the measured MRA frequency is 9.3 GHz with $Q_{MRA}$=2.2. Considering the $V_L$/R dependency, the calculated $V_L$ (~1420 m/s) is much lower than that of PnV. The reduction of the $V_L$ could be attributed to the fact that the influenza A virus is structurally not as compact as PnV (Noda, T. et al. Architecture of ribonucleoprotein complexes in influenza A virus particles. *Nature* 439, 490-492 (2006)) and has a soft lipid envelope ($V_L$~1500 m/s). Moreover, since the estimated $V_L$ and the mass density of influenza A viruses ($\rho$=1.2 g/cm$^3$) (*ICTVdB—The Universal Virus Database*, version 4, April 2006) are both close to those of water, the contrast of acoustic impedance is thus much smaller than that of PnV. This could explain why we observed a lower quality factor for Influenza A viruses. On the other hand, the MRA related to the high-order [SPH, l=1, n=1] acoustic mode also appears around 20 GHz with $Q_{MRA}$=2.3. It validates the dipolar activity of the high-order [SPH, l=1] mode.

WSSV

The bacillary WSSV was employed to check if the selection rules for the high-order-acoustic-mode MRA varies with the shape of virus. From the TEM image (FIG. 3*a*), the rod-shaped WSSV virions have an average length of 320 nm and an average diameter of 116 nm with a ±5% standard deviation ($Q_{MRA}$=10). Because of the large number of base pairs in the WSSV DNA (~60 times that of PnV and influenza A viruses), the MRA spectrum (FIG. 3*b*) shows strong absorption peaks at 8.6 GHz ($Q_{MRA}$=2.4), 25.5 GHz ($Q_{MRA}$=4.4), 39.5 GHz ($Q_{MRA}$=5.3), and 55 GHz ($Q_{MRA}$=5.6). As predicted by our proposed model on the rod-shaped virus, the peak frequency ratios are 1:3:5:7, corresponding to the dipolar-active confined longitudinal acoustic mode order N=2, 6, 10, and 14, respectively. Calculated from the MRA frequencies, $V_L$ of the WSSV is 2752 m/s, which is higher than that of PnV. This reflects the compressed nucleocapsids (540 nm long when released from virions (Tsai, J. M. et al. Identification of the Nucleocapsid, Tegument, and Envelope Proteins of the Shrimp White Spot Syndrome Virus Virion. *J. Virol.* 80, 3021-3029 (2006))) inside the intact WSSV virions which stiffen the virions and increase the speed of sound.

EV71

The EV71 (2R=28.5±1.5 nm) was investigated to see if the MRA spectroscopy can distinguish among the viruses having similar sizes and shapes. Comparing EV71's MRA spectrum (See FIG. 2*b*) with that of PnV, the MRA frequency of the [SPH, l=1, n=0] mode shifts a little bit higher to 43 GHz with a smaller MRA quality factor ($Q_{MRA}$=3.63). The change of MRA quality factor could originate from the different conditions of hydration on the surface of the virus (Van Zandt, L. L. Resonant microwave absorption by dissolved DNA. *Phys. Rev. Lett.* 57, 2085-2087 (1986)), which can be used to distinguish it from PnV. Aside from the confined-acoustic-phonon-related MRA, both PnV and EV71 show obvious absorption peaks around 60 GHz was also noted, which could arise from rotation of water molecules associated with functional groups of dissolved viruses (Webb, S. J., Booth, A. D. Absorption of microwaves by microorganisms. *Nature* 222, 1199-1200 (1969), Webb, S. J., Booth, A. D. Microwave absorption by normal and tumor cells. *Science* 174, 72-74 (1971)).

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cells, viruses, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A method for establishing a virus spectrum comprising (1) preparing a sample containing a purified known virus; (2) dropping the sample on a coplanar waveguide (CPW) circuit; (3) applying a microwave with frequencies ranging from 40 MHZ to 80 GHZ to the sample on the coplanar waveguide (CPW) circuit; (4) applying a network analyzer with frequencies ran in from 40 MHZ to 65 GHZ to simultaneously record reflection $S_{11}$ and transmission $S_{21}$ parameters of the CPW circuit; (5) evaluating an insertion power loss by $1-|S_{11}|^2-|S_{21}|^2$; and (6) obtaining an MRA spectrum under a dipolar acoustic mode of the virus by comparing insertion power loss spectra of the sample with and without the virus.

2. The method according to claim 1, wherein the known virus comprise Perina nuda viruses (PnV), influenza A viruses, bacillary white spot syndrome viruses (WSSV), and *enterovirus* 71 (EV71).

3. The method according to claim 1, wherein the MRA spectrum comprises an MRA frequency, MRA linewidth, and absorption selection rules of dipolar acoustic modes.

4. The method according to claim 1, further comprising steps for detecting or identifying a virus contained in a material to be detected by using the MRA spectrum under a dipolar acoustic mode of the known virus of claim 1, the steps comprising: (1') preparing the material to be detected; (2') using steps (2), (3), (4), (5) and (6) of claim 1 to obtain a MRA spectrum under a dipolar acoustic mode of the material to be detected; (3') comparing the MRA spectrum under a dipolar acoustic mode of the detected material with the MRA spectrum under a dipolar acoustic mode of the known virus of claims 1; and (4') identifying the virus of the material to be detected.

5. The method according to claim 4, wherein the material to be detected is a biological sample from a subject.

6. A method according to claim 4, wherein the MRA spectrum comprises an MRA frequency, MRA linewidth, and absorption selection rules of dipolar acoustic modes.

* * * * *